United States Patent [19]

Kajiura et al.

[11] Patent Number: 4,912,318
[45] Date of Patent: Mar. 27, 1990

[54] INSPECTION EQUIPMENT FOR SMALL BOTTLES

[75] Inventors: Toshihiro Kajiura, Osaka; Norio Oita, Kobe; Naohide Asari, Osaka, all of Japan

[73] Assignee: Kanebo Ltd., Tokyo, Japan

[21] Appl. No.: 226,821

[22] Filed: Aug. 1, 1988

[30] Foreign Application Priority Data

| Aug. 4, 1987 [JP] | Japan | 62-195623 |
| Nov. 30, 1987 [JP] | Japan | 62-303562 |
| Mar. 4, 1988 [JP] | Japan | 63-29519 |
| May 18, 1988 [JP] | Japan | 63-122767 |

[51] Int. Cl.$^4$ .................. B07C 5/342; G01N 21/00
[52] U.S. Cl. .................. 250/223 B; 209/526; 356/240
[58] Field of Search .......... 250/223 B; 209/524, 209/526, 525, 576, 577, 588; 356/240

[56] References Cited

U.S. PATENT DOCUMENTS

| 3,411,009 | 11/1968 | Ford et al. | 209/524 |
| 4,378,493 | 3/1983 | Dorf et al. | 250/223 B |
| 4,636,635 | 1/1987 | Kronseder | 209/526 |

FOREIGN PATENT DOCUMENTS

| 2166236 | 8/1973 | Fed. Rep. of Germany | 209/526 |
| 57-11416 | 3/1982 | Japan. | |
| 59-183351 | 10/1984 | Japan. | |

Primary Examiner—Edward P. Westin
Attorney, Agent, or Firm—Stevens, Davis, Miller & Mosher

[57] ABSTRACT

Inspection equipment for inspecting products including medicines such as phials and ampuls and foods such as drinking water. The products are placed on the pedestals of an indexing turn table to be intermittently transferred. The products are held on their peripheral surface by a disk turn table and a pair of rollers and rotated on their own axes by the turn of the disk turn table. The products intermittently transferred are lighted on their surface to be inspected for each stop, inspected by being imaged with an imaging device, and sorted into a nondefective products group and a defective products group with a sorting device.

3 Claims, 9 Drawing Sheets

11A–11G = LIGHTING DEVICES
12A–12G = IMAGING DEVICES

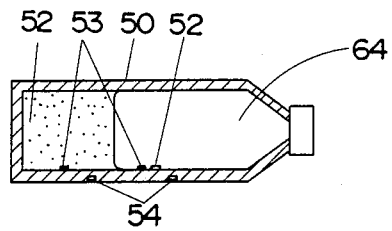
Fig. 15A
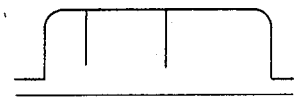
Fig. 15B
Fig. 16  PRIOR ART       Fig. 17
                         PRIOR ART
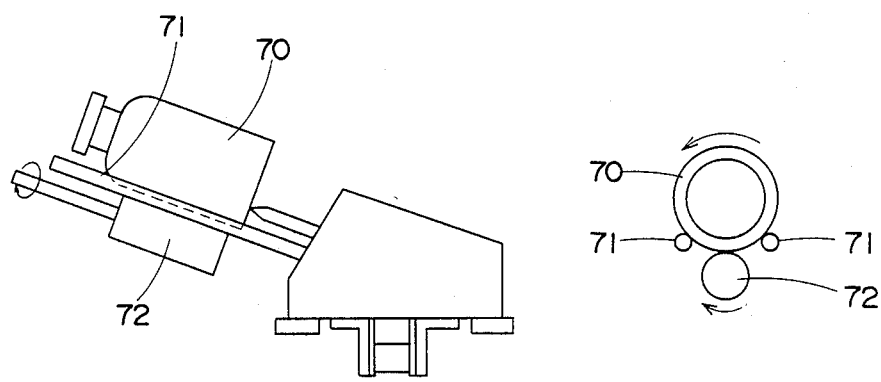

INSPECTION EQUIPMENT FOR SMALL BOTTLES

BACKGROUND OF THE INVENTION

This invention relates to inspection equipment for inspecting mainly bottled products and cylindrical products such as medicines (phials and ampuls) and foods (bottled drinking water) for appearance, dimension and defect.

Up to now, a variety of inspection equipments has been proposed to inspect for foreign matter in ampuls and phials. For example, Japanese Patent laid-open publication No. 11416/1982 discloses inspection equipment which rotates rapidly a transparent container filled with a liquid, then suddenly stops the container, irradiates a light beam to the container, receives the light beam by a light detector behind the container, and detects foreign matter which is kept rotated and suspended within the contained liquid Japanese Patent laid-open publication No. 183351/1984 also discloses ampul inspection equipment which rotates rapidly an ampul with the axis of the ampul being as a rotation center while the ampul is held by a pair of upper and lower holders of an inspection drum, the equipment then suddenly stops the ampul, and inspects the ample for nondefective or defective product while the ample is irradiated with a transmission light beam in a specified direction to be imaged by a television camera.

However, in the inspection equipment disclosed by the above patents, the transparent container and ampul must be held from their upper and lower side by a holder to rotate and transfer them. Thus the ampul has not been able to be inspected from its upper and lower side, making an appearance test over its whole surface impossible. The holder also has obstructed inspection such that a lighting device has not been able to approach near these products to cause a high-brightness and uniform lighting over their whole surface to become possible, leading to difficulty in performing a high-accuracy inspection.

Inspection equipment to inspect phials has been placed on the market. The equipment, as shown in FIGS. 16 and 17, holds a phial 70 by a pair of bars 71 and 71 with the phial assuming a inclined posture, allows a rotating roll 72 to rotate on the side of the phial 70, arranges a large number of the phials 70 in a line while the phials 70 are allowed to be rotated, and transfers them continuously to an inspection station where visual inspection is performed.

However, in such transfer arrangement, the phial 70 has been held on its side, so that the held part of the phial has not been able to be inspected and the phial has had the possibility of being crushed when inspected due to insufficient holding of the phial 70. For this reason, the equipment has not been able to be used for automatic inspection.

SUMMARY OF THE INVENTION

A major object of the invention is to provide inspection equipment which can sequentially transfer a large number of the products to be inspected while they are held stably at an inspection station.

Another object of the invention is to provide an inspection equipment which can inspect nearly the whole surface of the products to be inspected.

A further object of the invention is to provide inspection equipment which lights the products to be inspected at n inspection station under a high-brightness and uniform lighting condition to make a high-accuracy inspection possible.

In accordance with the invention, inspection equipment is provided which comprises an indexing turn table turning intermittently in one direction and having a plurality of pedestals for placing the products to be inspected arranged at certain intervals along the outer peripheral edge of the table; a disk turn table arranged concentrically on the indexing turn table, turning on the same axis and for making the products to be inspected rotated on their own axes by contacting the outer peripheral surface of the disk turn table with the peripheral surface near the bottom of the products placed on said pedestals; a pair of rollers spaced from each other on both side positions of said pedestals and on the outside of said disk turn table, for holding said products placed on the pedestals of said indexing turn table and having the outer peripheral surface of the rollers contacted with the peripheral surface near the bottom of the products; a star wheel partly overlapped with said indexing turn table and interlocked with the intermittent turn of the indexing turn table to supply the products to be inspected to the indexing turn table at the first crossing area with the table and to recover the products from the indexing turn table at the second crossing area; a plurality of lighting devices arranged along the peripheral direction of said indexing turn table for each stop position of said pedestals associated with the intermittent turn of the indexing turn table and for lighting the surface to be inspected of said products placed on the pedestals; a plurality of imaging devices for imaging each surface to be inspected of said products lighted by these lighting devices to output image signals; an image processing device for processing the image signals outputted from the imaging devices to generate the defective signals associated with the products; and a sorting device placed near said star wheel and for responding to said defective signals among the products to be inspected recovered by the star wheel selectively to sort out defective products.

BRIEF DESCRIPTION OF THE DRAWING

FIG. 15 A and FIG. 15 B are illustrative views showing a product being inspected and the wave form observed when the product is lighted by the lighting devices indicated in FIG. 12, and FIG. 16 and FIG. 17 are side and front views showing a conventional, visual appearance inspection equipment.

DETAILED DESCRIPTION OF THE PREFERRED EMBODIMENT

Figure 1:
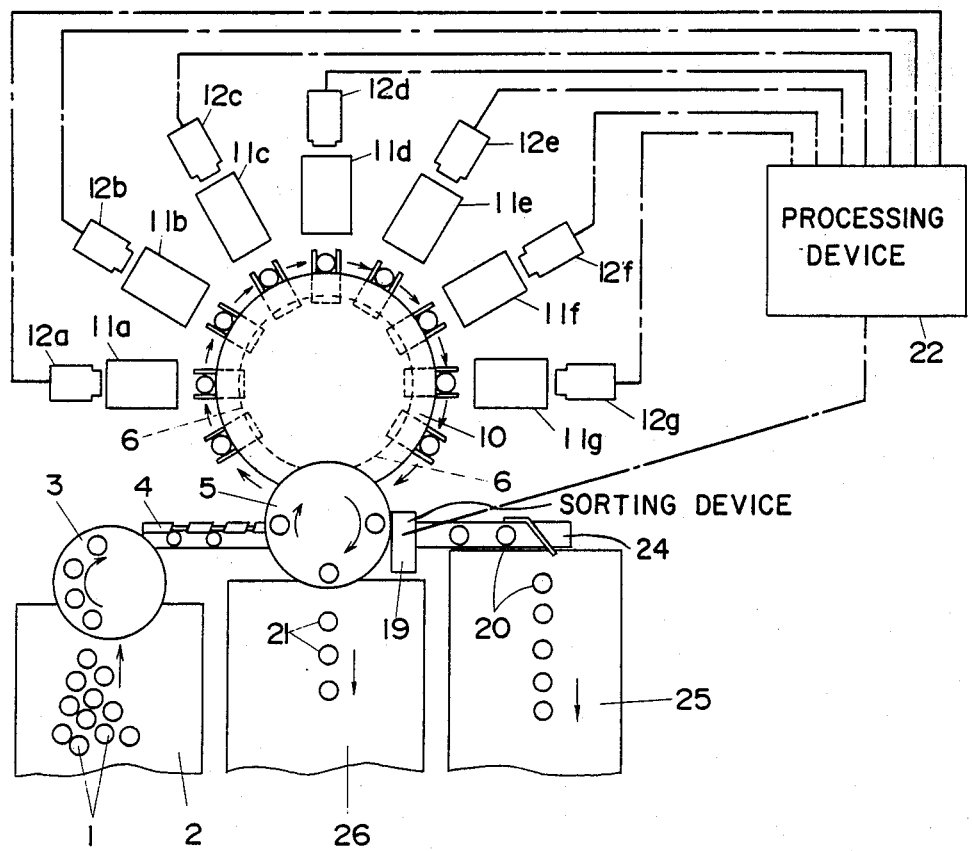
FIG. 1 is an outline plan view showing an embodiment of the inspection equipment according to the invention.

The inspection equipment is designed to inspect phials as products to be inspected. As shown in FIG. 1, the edge of a supply conveyor 2 for supplying products to be inspected 1 is provided with a straightening table 3 through which screw feeder 4 is connected. Said straightening table 3 makes the products 1 arranged in a line and transfers them to the screw feeder 4. The screw feeder 4 transfers sequentially the products 1 to a star wheel 5 at certain intervals.

The star wheel 5 turns intermittently in one direction, has a plurality of transfer pockets 5a around the wheel at certain intervals and holds the goods 1 in the transfer pockets 5a. The star wheel 5 is partially overlapped with an indexing table 6 and interlocked with it to be turned intermittently.

Figure 3:
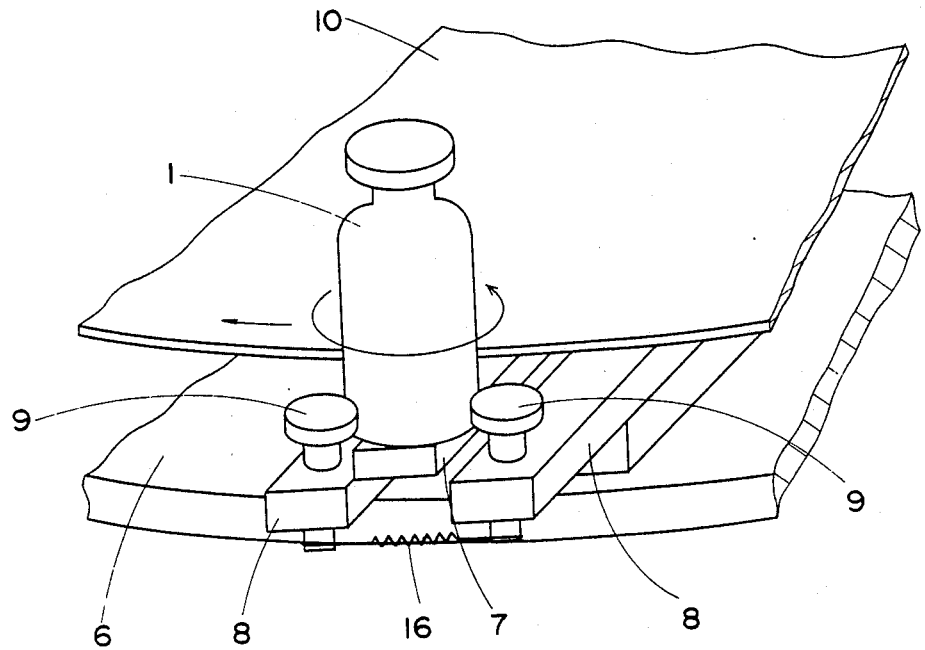
FIG. 3 is a perspective side view, with part broken away and in section, showing the holding mechanism for the products to be inspected.

The indexing table 6 has a plurality of product placing pedestals 7 projected radially from the outer peripheral edge along the full circumference as shown in FIG. 3. The pedestals 7 are made of a material with a low friction resistance such as ceramic with consideration to the slidability of the products 1 rotating on their own axes. A pair of arms 8 and 8 are arranged on both sides of the pedestals 7, and rollers 9 and 9 of which each outer peripheral surface is in contact with the peripheral surface of the product 1 are mounted on the upper face of the edge of these arms 8 and 8. In said arms 8 and 8, the edges are approachably and specially mounted each other, and a spring 16 is tightly provided between these edges to actuate said rollers 9 and 9 in the direction such that the rollers approach each other.

A disk turn table 10 which is arranged concentrically on the indexing turn table 6, has a larger radius than that of the table 6 and is in contact with said goods 1 with its outer peripheral surface is provided above the indexing turn table. Thus, the product 1 is held at the peripheral surface near its bottom by the rollers 9 and 9 and the disk turn table 10, and rotates on its own axis by the turn of the disk turn table 10.

Figure 2:
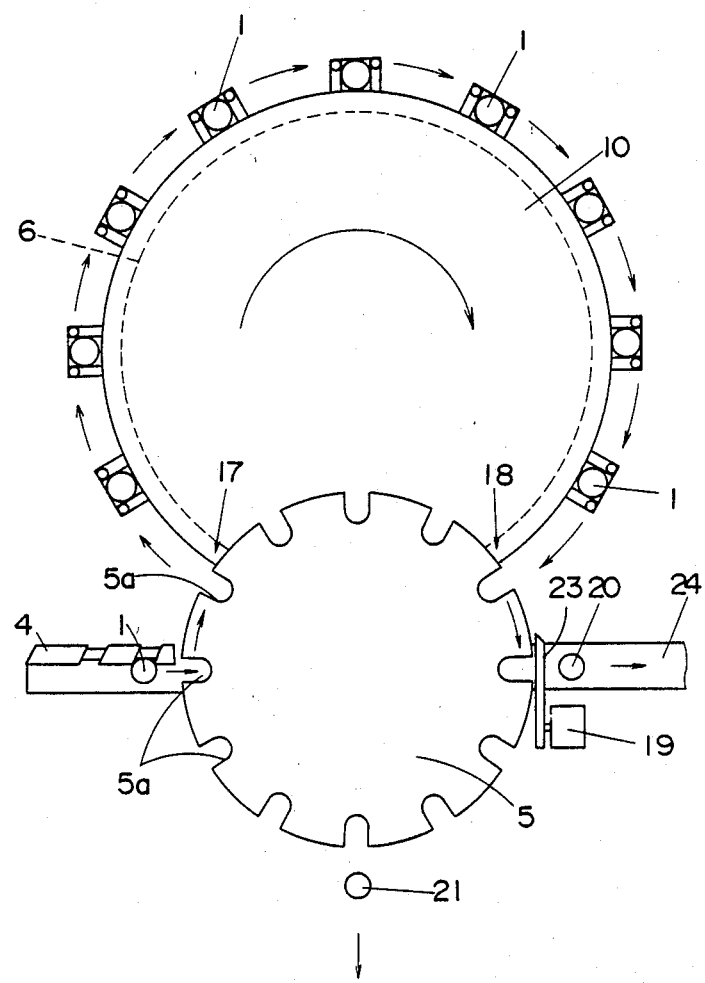
FIG. 2 is a plan view showing the principal part of FIG. 1.

The product 1 is supplied from said star wheel to the pedestal 7 in such a manner that, as shown in FIG. 2, when the transfer pocket 5a holding the product 1 approaches the first crossing area 17 where the indexing turn table 6 crosses with the star wheel 5, the pocket places the product 1 on the pedestal 7 by pushing open the said pair of rollers 9 and 9 and then the indexing turn table 6 begins to turn intermittently to remove the product 1 from the start wheel 5.

Said indexing turn table which is a disk turned intermittently in one direction repeats a turn and stop notion each for a certain time. As shown in FIG. 1, lighting devices 11a through 11g and imaging devices 12a through 12g (line sensor cameras, etc ) are arranged on the stop positions of the pedestals 7 forming an inspection station. Each of the lighting devices 11a through 11g lights a respective surface to be inspected of the products 1, and the imaging devices 12a through 12g image respective surface to be inspected. Where the products 1 are phials, the cap top face, head side, shoulder side of containers, side, surface of contents, and bottom face can be inspected. The surface to be inspected is properly selected according to the object of inspection and is not specifically limited.

Each of the lighting devices 11a through 11g is, composed so as to light clearly the surface to be inspected of the product 1 using one or two or more optical fiber bundles. A preferred arrangement of the lighting devices is described hereinafter.

Figure 4A:
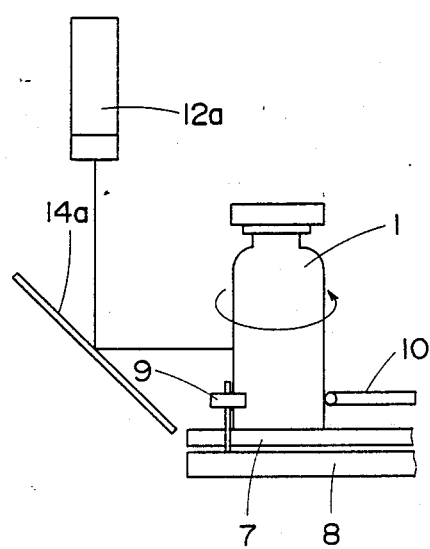
FIG. 4 A and FIG. 4 B are outline side and front views showing the imaging mechanism for the side of the products.
Figure 4B:
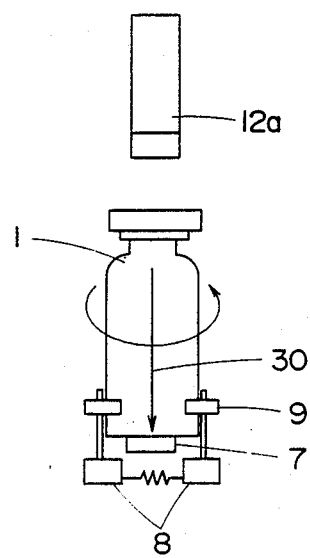
Figure 5A:
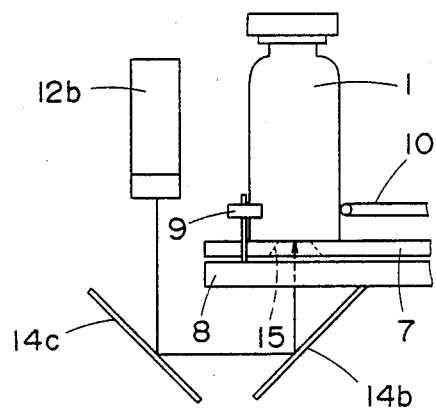
FIG. 5 A and FIG. 5 B are outline side and bottom end views showing the imaging mechanism for the bottom of the products.
Figure 5B:
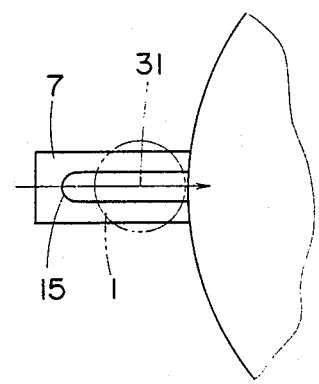

FIG. 4 A shows the position of the imaging device 12a to inspect the side of the product 1, where the product 1 is imaged through a mirror 14a provided on the forward side. In FIG. 4 B, an arrow 30 indicates the inspection line of the imaging device 12a in FIG. 4 A. FIG. 5 A shows the position of the imaging device 12b to inspect the bottom face of the product 1, where the product 1 is imaged through a slit 15 provided on the bottom of the product 1 and then mirrors 14b and 14c on the lower side. In FIG. 5 B, an arrow 31 is the inspection line of the imaging device 12b in FIG. 5 A.

Figure 6:
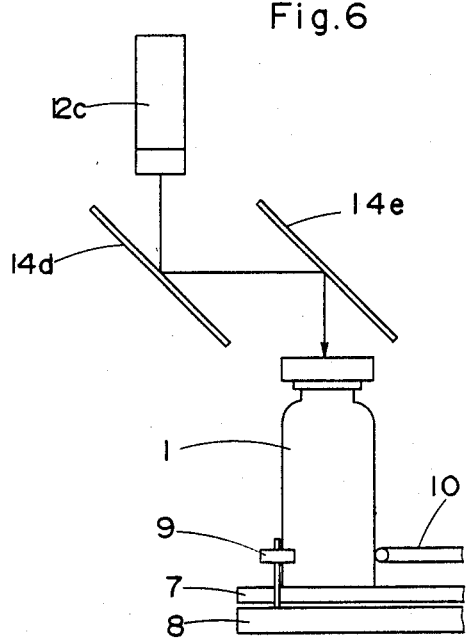
FIG. 6 is an outline side view showing the imaging mechanism for the upper face of the products.

FIG. 6 shows the inspection of the upper face of the product 1, where the upper face of the product 1 is imaged by the imaging device 12c and mirrors 14d and 14e.

Thus, the product 1 is held by being nipped at the peripheral surface near its bottom by said pair of rollers 9 and 9 and the disk turn table 10, and is rotated on its own axis by the turn of the disk turn table 10. As a result, the holding of the product 1 becomes stable and any surface to be inspected of the product 1 can be lighted with a high-brightness and uniform lighting in a required direction, allowing the whole surfaces to be inspected.

The product 1 whose inspection has been finished at each inspection station, as shown in FIG. 2, is received by the transfer pocket 5a of the star wheel 5, and then the star wheel 5 turns intermittently in the direction so as to remove the product 1, allowing the product 1 to be removed from the pedestal 7. The product 1 recovered by the transfer pocket 5a is sorted into a nondefective product group 20 of a defective product group 21 by a sorting device 19.

That is, as shown in FIG. 1, the image signals outputted from said imaging devices 12a pl through 12g are processed by an image processing device 22, and when the product 1 is judged to be a nondefective product, the nondefective product 20 is discharged from the start wheel 5 through a nondefective product discharge belt 24 by opening a gate 23 provided on the sorting device 19 (see FIG. 2), and then is transferred by a nondefective product discharge conveyor 25 to the next process. On the other hand, if judged to be a defective product, the defective product is passed through by closing the gate 23 responding to defective signals, and then is discharged by a defective product discharge conveyor 26.

Thus, the product 1 is passed from the screw feeder 4 through the star wheel 5, placed on the pedestal 7 of the indexing turn table 6, inspected, recovered by the same star wheel 5, and then sorted by the sorting device 19, so that the compact design of the equipment can be planned and the product 1 stably transferred.

A preferred lighting device according to the invention is described hereinafter.

Figure 7:
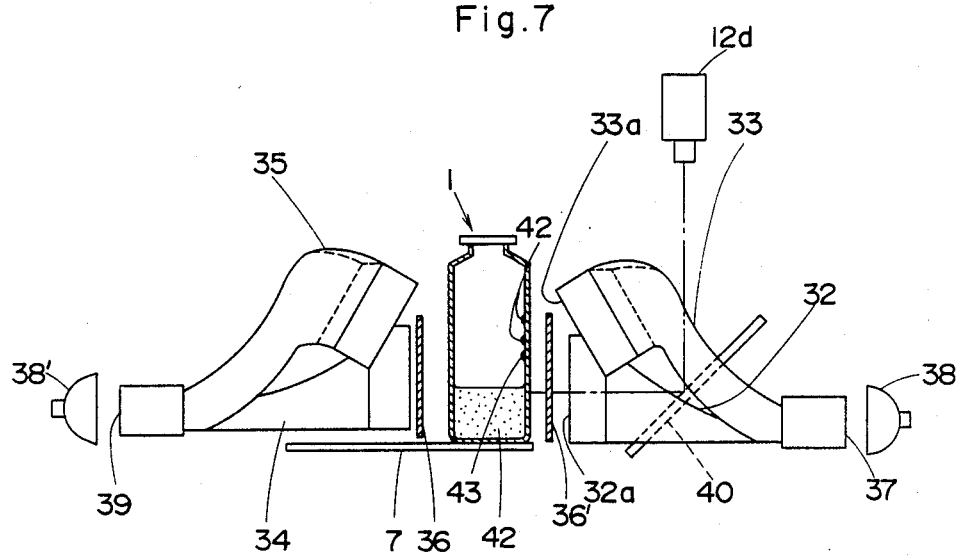
FIG. 7 is a perspective side view, with parts broken away and in section, showing preferred lighting devices of the invention.
Figure 8:
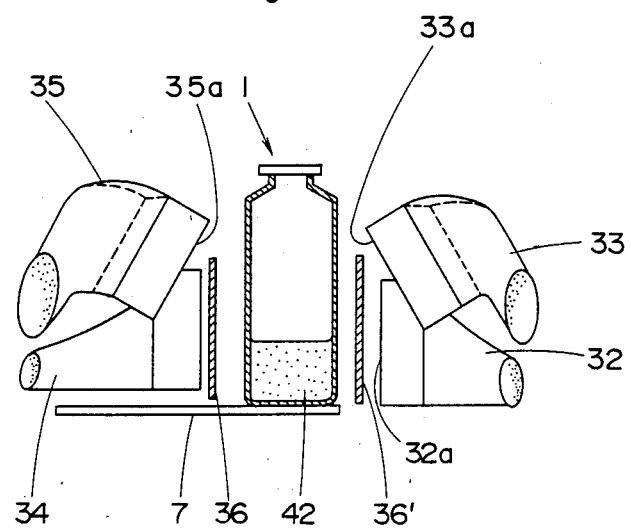
FIG. 8 and FIG. 9 are side and plan views showing the three-dimensional arrangement of the optical fiber bundles in FIG. 7.
Figure 9:
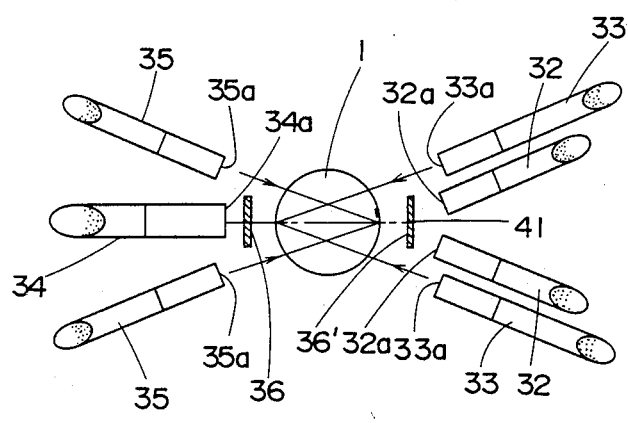

FIG. 7 shows a lighting device using optical fiber bundles, and FIG. 8 and FIG. 9 show the three-dimensional arrangement of optical fiber bundles.

As shown in FIG. 7, the product to be inspected 1 placed on the pedestal 7 contains a powder 42 such as powder injection, and a part of the powder 42 and foreign matter adhere to the upper wall.

An optical fiber bundle 32 for reflection lighting and an optical fiber bundle 33 for uniform lighting are provided on the imaging side of the product 1, and an optical fiber bundle 34 for transmission lighting and an optical fiber bundle 35 for uniform lighting are provided on the opposite side. Diffuse transmission members 36 and 36' are between the optical fiber bundle 34 for transmission lighting and the product 1 and between the optical fiber bundle 32 for reflection lighting and the product 1, respectively. The diffuse transmission members 36 and 36', are, for example common typing paper, transmission plastic sheet or film, and function so as to diffuse the light from the optical fiber bundles 32 through 35 and thus lead to uniform lighting of the product 1. In this case, the diffuse transmission member 36 lying between the product 1 and the optical fiber bundle 32 for reflection lighting is not always required and can be omitted. However, the diffuse transmission member 36' prevents the glitter due to diffused reflection from the product 1 and to contribute further to the uniform lighting and the high-brightness per unit area, so that it is preferred to provide such member 36'.

Said optical fiber bundle 32 for reflection lighting has a light receiving part 37 arranged on the front side of a light source 38, and has two-divided light projecting parts 32a and 32(see FIG. 9) by which the imaging side surface of the product 1 is reflection lighted. The optical fiber bundle 33 for uniform lighting on the imaging side uses the same light receiving part 37 and is defined by being divided from the optical fiber bundle 32 for reflection lighting.

On the other hand, the optical fiber bundle 34 for diffuse transmission has a light receiving part 39 arranged on the front side of a light source 38'. The optical fiber bundle 35 for uniform lighting uses the same light receiving part 39 and is divided from the optical fiber bundle 34 for transmission lighting.

A mirror 40 is arranged on the front of the imaging side of the product, and the imaging divide 12d is provided above the mirror 40 to image the product 1 reflected by the mirror 40.

As shown in FIG. 8 and FIG. 9, the imaging side surface of the product 1 is reflection lighted by the light projecting parts 32a and 32a of the optical fiber bundle 32 for reflection lighting, on the each side of which the respective light projecting part 33a of the optical fiber bundles 33 and 33 for uniform lighting is positioned. On the opposite side, as shown in FIG. 9, a light projecting part 34a of the optical fiber bundle 34 for transmission lighting is provided on the place to which an imaging slit 41 provided in the diffuse transmission member 36' on the imaging side is linearly opposed through the product 1. On the each side of the light projecting part, light projecting parts 35a and 35a of the optical fiber bundles 35 and 35 for uniform lighting are positioned.

The product 1 is reflection lighted from the imaging side by the optical fiber bundle 32 for reflection lighting, and transmission lighted from the opposite side by the optical fiber bundle 34 for transmission lighting. In this case, if the intensity of reflection light of the product 1 is set to be equal to that of transmission light, the presence of a defect (such as dirt and foreign matter) differing in clearness from a nondefective product can be detected by image processing the product 1 imaged. Accordingly, even if the powder contained in the product 1 adheres to the wall of the container, the distinguishment between defect and powder can be easily determined. Particularly, the optical fiber bundles 32 and 34 allow the light projecting parts 32a and 34a of them to be approached to the extent that the lighting balance may not be broken, and the product 1 to be lighted with a high-brightness, and further, the optical fiber bundle 32 for reflection lighting has the plurally divided light projecting parts 32a through 35a to reflection light in various directions, thereby providing uniform lighting.

Also, the optical fiber bundles 33 and 35 for uniform lighting arranged on the imaging side and opposite side of the product 1, as shown with the arrows in FIG. 9, are arranged such that the front and back wall surfaces of the product 1 are spot lighted from the imaging side and the opposite side of the product 1, respectively. Thus, the front surface of the imaging side is reflection lighted in forward and backward directions, allowing a uniform lighting without shadow, regardless of the amount of contents. Accordingly, the defect present in the portion in which the powder 42 is contained in the product 1 can also be simultaneously detected. The optical fiber bundles 33 and 35 for uniform lighting are for spot lighting, so that the interposition of a diffuse transmission member is not required.

Figures 10A, 10B, 11A, 11B:
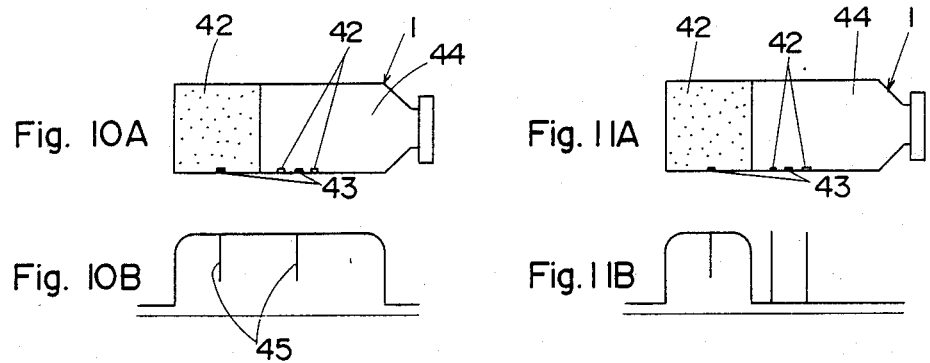
FIG. 10 A and FIG. 10 B are illustrative views showing the relationship between a product being inspected and the wave form observed when the product is lighted by the lighting device in FIG. 7.
FIG. 11 A and FIG. 11 B are illustrative views showing a product being inspected and the wave form observed by a conventional reflection type lighting.

FIG. 10 A and FIG. 10 B show the product 1 and the related wave form observed by imaging and image processing the product 1, respectively. In FIG. 10 A, defects 43 (such as dirt and foreign matter) are present on the wall in the portion in which the powder 42 is contained and in a cavity portion 44, respectively, in the product 1 such as a phial. At this time, a part of the powder 42 adheres to the wall of the cavity 44. Under such condition, when the product 1 is lighted by the lighting devices for inspection shown in FIG. 7 through FIG. 9 to be imaged and appearance inspected, the wave form obtained is uniform regardless of the portion contained with the powder 42 and of the cavity portion 44, allowing only the presence of the defects 43 to be evidently detected (in FIG. 10 B, numerals 45 the presence of defects).

On the contrary, by a conventional reflection-type lighting device only, as shown in FIG. 11 A and FIG. 11 B, the distinguishment between the powder adhering to the wall and the defects 43 can not be determined. Further, since the amount of the powder 42 is not constant, the distinguishment between the powder and the defects is hardly determined on the wave form observed by the appearance inspection through the side surface, obstructing the automation of inspection.

Figure 12:
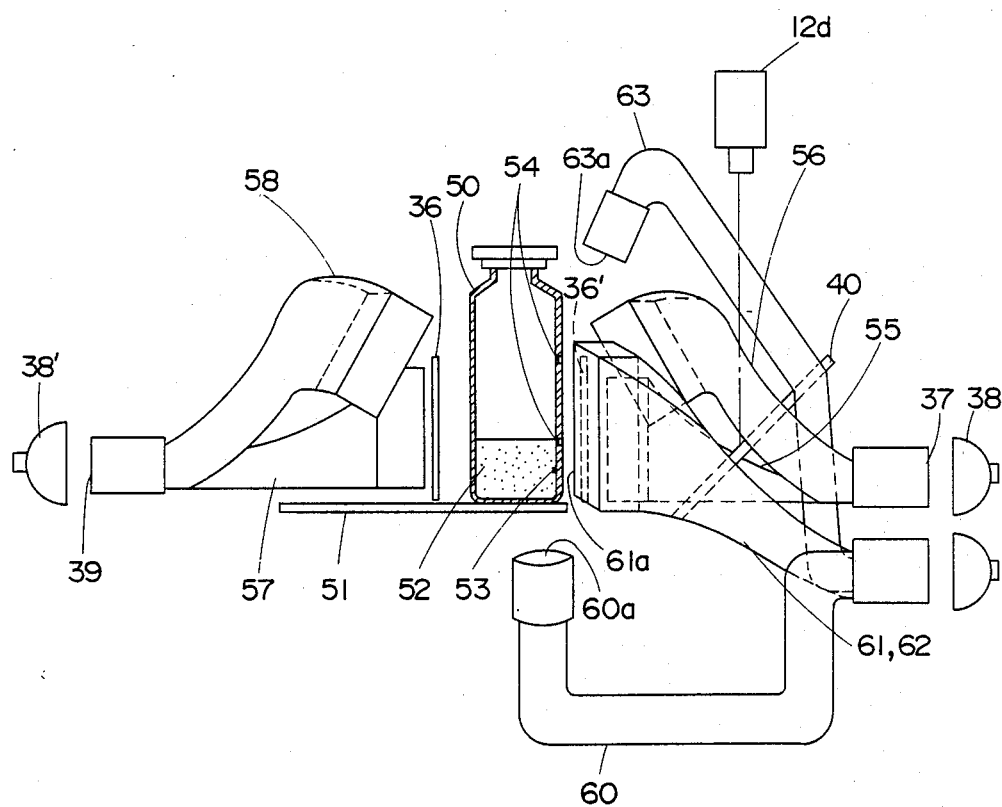
FIG. 12 is a perspective side view showing other lighting devices according to the invention.
Figure 13:
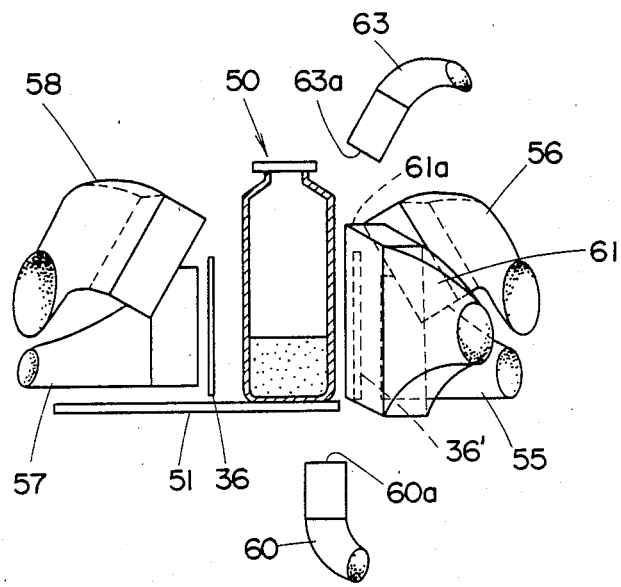
FIG. 13 and FIG. 14 are side and plan views showing the three-dimensional arrangement of the optical fiber bundles in FIG. 12.
Figure 14:
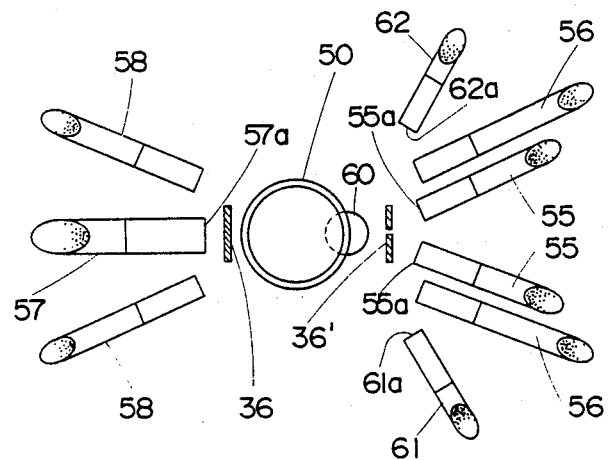

With reference to FIG. 12 through FIG. 14, the preferred lighting device is hereinafter described. The lighting device is obtained by improving and developing the lighting device shown in FIG. 7 through FIG. 9 so as to be suitably applied to the containers, in particular, such as phials and ampuls. That is, the lighting devices mentioned above have a possibility of misunderstanding such that, if air bubbles are present inside the wall of a container made of glass and the like, a shadow develops on a part of the air bubbles, causing the device to misunderstand the shadow as a defect. Accordingly, the device is designed to perform a high-accuracy inspection even if such air bubbles are present.

The explanation for the same members as shown in FIG. 7 through FIG. 9 is omitted but the same reference numerals are used.

As shown in FIG. 12, a container 50 to be inspected is placed on a pedestal 51. Powder 52 such as injection powder is contained in the container 50, a defect 53 adheres to the wall of the container, and air bubbles 54 are present inside the wall.

An optical fiber bundle 55 for reflection lighting and an optical fiber bundle 56 for uniform lighting are provided on the imaging side of the container 50, and an optical fiber bundle 57 for transmission lighting and an optical fiber bundle 58 for uniform lighting provided on the opposite side, respectively. Also, the diffuse transmission member 36' lies between the optical fiber bundle 55 and the container 50, and the diffuse transmission member 36 lies between the optical fiber bundle 57 for transmission lighting and the container 50 (see FIG. 13).

On the other hand, as shown in FIG. 12 through FIG. 14, respective light projecting parts 60a through 63a of optical fiber bundles 60 through 63 for auxiliary lighting are arranged on the upper and lower sides and on the both sides with respect to the imaging region of the container 50. The direction of the light projection parts 60a through 63a is set at a certain angle to the imaging direction so that light may enter inside the wall in the imaging region of the container 50. That is, the light projecting part 60a arranged under the container 50 is positioned just under the imaging region of the container 50 so that light may pass through an opening (not illustrate) and inside the wall. The upper light projecting part 63a is installed at the position slightly inclined forward from the vertical line. This is because of difficulty in lighting in vertical direction. Although even at such position a part of the light reflects on the surface of the container 50, the remaining light enters inside the wall in the imaging region of the container 50. The light from the light projecting parts 61a and 62a on the both sides is irradiated in similar manner to the above. The most basic irradiation among the irradiations in these four direction is the one from the lower light projecting part 60a, in which case the light is allowed to pass inside the wall with little loss of light intensity.

Thus, light is allowed to enter inside the wall in the imaging region of the container 50, so that, even if the air bubbles 54 are present inside the wall, light is irradiated to the peripheral part of the shade-prone air bubbles 54 to allow the shade of the air bubbles to be nearly dissipated. As a result, the air bubbles 54 and defect 53 can be easily distinguished. FIG. 15 A and FIG. 15 B show the container 50 and the related wave form observed by imaging and image processing the container 50, respectively. In FIG. 15 A, defects 53 are present in the portion in which the powder 52 is contained and in a cavity portion 64, respectively, in the container 50. Also, a part of the powder 52 adheres to the wall of the cavity portion 64, and the air bubbles 54 are present inside the wall. Under such condition, when the container 50 is irradiated by the lighting device for inspection shown in FIG. 12 through FIG. 14 to be imaged and appearance inspected, the wave form obtained allows the presence of the defects 53 only to be evidently detected regardless of the contained powder 52 and the air bubbles 54.

Thus, light is allowed to enter inside the wall in the imaging region of the container 50 by using the optical fiber bundles 60 through 63 for auxiliary lighting, so that the shadow of the air bubbles inside the wall is dissipated to allow the air bubbles and the defect to be easily distinguished.

Accordingly, inspection accuracy is improved and a high-speed appearance inspection becomes practical.

Although the lighting device mentioned previously is one of the plurality of the lighting devices used for the inspection equipment according to the invention, other lighting devices also can provide a uniform lighting by optionally combining the optical fiber bundles.

What is claimed is:

1. Inspection equipment for inspecting cylindrical products such as phials for appearance, dimension and defects comprising:
   an indexing turn tale mounted for turning intermittently in one direction and having plurality of pedestals for placing the products to be inspected arranged at predetermined intervals along the outer peripheral edge of the table;
   a disk turn table arranged concentrically on the indexing turn table, turning on the same axis and mounted for causing the products on the pedestals to rotate on their own axes by contacting the outer peripheral surface of the disk turn table with the peripheral surface of the product near the bottom thereof;
   a pair of rollers spaced from each other and positioned on both sides of said pedestals and on the outside of said disk turn table, for holding said products placed on the pedestals of said indexing turn table and having the outer peripheral surface of the rollers contacted with the peripheral surface of the products near the bottom thereof;
   a star wheel partly overlapping said indexing turn table and interlocked with the intermittent turn of the indexing turn table to supply said products to the indexing turn table at a first crossing area with the indexing turn table and to recover the products from the indexing turn table a second crossing area between the star wheel and the indexing turn table;
   a plurality of lighting devices arranged along the periphery of siad indexing turn table for each stop position of siad pedestals associated with the intermittent turn of the indexing turn table and for lighting the surface to be inspected of said products placed on the pedestals;
   a plurality of imaging devices for imaging each surface to be inspected of siad product slighted by these lighting devices so as to output image signals from the imaging devices;
   an image processing device for processing the image signals outputted from the imaging devices to generate a defective signal associated with siad products; and
   a sorting device placed near said star wheel and for responding to said defective signals amount the products recovered by the star wheel to sort out defective products.

2. The equipment of claim 1, wherein one of said lighting devices comprises;

an optical fiber bundle for reflection lighting having a plurality of light projecting parts which reflection light one side surface of the products to be inspected, thus defining an imaging side surface portion of said product;

an optical fiber bundle for transmission lighting having light projecting parts arranged on the side opposite to the imaging side of aid products and for transmission lighting the products;

an optical fiber bundle for uniform reflection lighting of said products from both the imaging side and the opposite side; and a diffuse transmission member lying between said products and said optical fiber bundle for transmission lighting.

3. The equipment of claim 1, wherein said products to be inspected are transparent or semitransparent containers; and one of said lighting devices comprises an optical fiber bundle for reflection lighting having a plurality of light projecting parts which reflection light one side surface of said container at these light projecting parts, thus defining an imaging side surface portion of said container, an optical fiber bundle for transmission lighting having light projection parts arranged on the side opposite to the imaging side of said container to transmission light the container, and an optical fiber bundle for auxiliary lighting to light the container in a direction at a certain angle to the container so that light may enter inside the transparent or semitransparent wall along the imaging side surface portion of said container.

* * * * *